US008822152B2

(12) United States Patent
van de Wiel et al.

(10) Patent No.: US 8,822,152 B2
(45) Date of Patent: Sep. 2, 2014

(54) MULTIPLEX NUCLEIC ACID AMPLIFICATION USING BLOCKED PRIMERS

(75) Inventors: Paul van de Wiel, Quaix en Chartreuse (FR); Birgit Deiman, Oisterwijk (NL); Dianne van Strijp, Hertogengbosch (NL)

(73) Assignee: bioMerieux B.V., AB Boxtel (NL)

( * ) Notice: Subject to any disclaimer, the term of this patent is extended or adjusted under 35 U.S.C. 154(b) by 1160 days.

(21) Appl. No.: 12/513,955

(22) PCT Filed: Nov. 7, 2007

(86) PCT No.: PCT/EP2007/009715
§ 371 (c)(1),
(2), (4) Date: Oct. 2, 2009

(87) PCT Pub. No.: WO2008/055691
PCT Pub. Date: May 15, 2008

(65) Prior Publication Data
US 2010/0143882 A1    Jun. 10, 2010

(30) Foreign Application Priority Data
Nov. 10, 2006 (EP) .................................... 06023431

(51) Int. Cl.
*C12Q 1/68* (2006.01)
*C12P 19/34* (2006.01)
(52) U.S. Cl.
CPC .................... *C12Q 1/6865* (2013.01)
USPC ......... 435/6.12; 435/6.1; 435/6.11; 435/91.1; 435/91.2; 435/91.21
(58) Field of Classification Search
CPC ................................................... C12Q 1/6865
See application file for complete search history.

(56) References Cited

U.S. PATENT DOCUMENTS

| 5,480,784 A | * | 1/1996 | Kacian et al. | 435/91.21 |
| 6,057,134 A | * | 5/2000 | Lader et al. | 435/91.2 |
| 2006/0046265 A1 | * | 3/2006 | Becker et al. | 435/6 |

FOREIGN PATENT DOCUMENTS

WO    WO 94/03472    2/1994

OTHER PUBLICATIONS

Jean et al., "Simultaneous detection and identification of hepatitis A virus and rotavirus by multiplex nucleic acid sequence-based amplification (NASBA) and microtiter plate hybridization system," Journal of Virological Methods, 2002, vol. 105, pp. 123-132.*
Chan and Fox "NASBA and Other Transcription-Based Amplification Methods for Research and Diagnostic Microbiology" *Reviews in Medical Microbiology* 10(4):185-196 (1999).
Greijer et al. "Multiplex Real-Time NASBA for Monitoring Expression Dynamics of Human Cytomegalovirus Encoded 1E1 and pp67" *Journal of Clinical Virology* 24:57-66 (2002).
International Search Report and Written Opinion for International Application No. PCT/EP2007/009715, mailed Mar. 7, 2008 (12 pages).

* cited by examiner

*Primary Examiner* — Young J Kim
(74) *Attorney, Agent, or Firm* — Myers Bigel Sibley & Sajovec, PA

(57) ABSTRACT

The present invention is in the field of nucleic acid amplification, and in particular in transcription-based amplification, providing improvements thereof. Specifically, the present invention provides primers, and methods for using them, that improve transcription-based amplification reactions, in particular multiplex reactions.

19 Claims, 5 Drawing Sheets

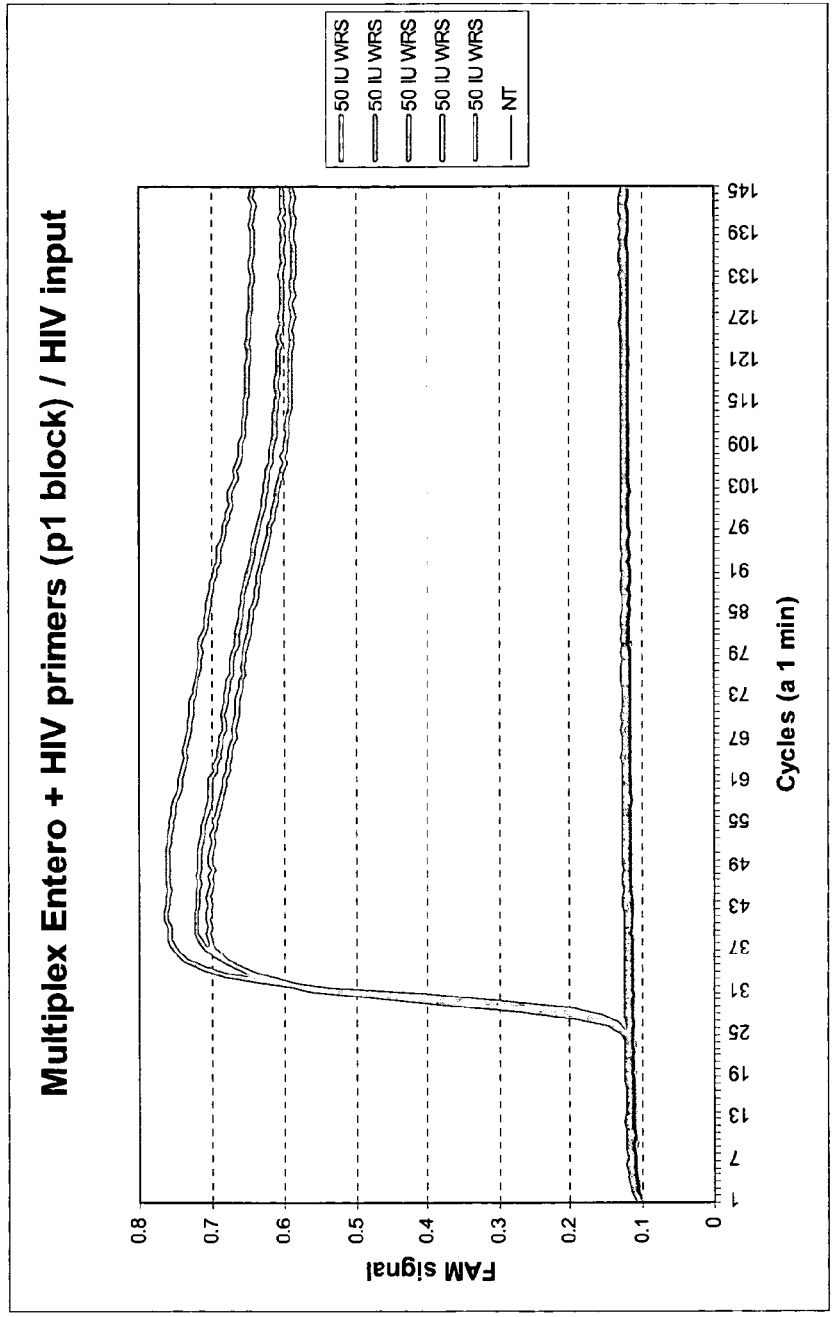

SEQUENCE LISTING

```
<160> NUMBER OF SEQ ID NOS: 19

<210> SEQ ID NO 1
<211> LENGTH: 24
<212> TYPE: DNA
<213> ORGANISM: Artificial
<220> FEATURE:
<223> OTHER INFORMATION: T7 polymerase promoter

<400> SEQUENCE: 1
aatttaatac gactcactat aggg                                           24

<210> SEQ ID NO 2
<211> LENGTH: 25
<212> TYPE: DNA
<213> ORGANISM: Artificial
<220> FEATURE:
<223> OTHER INFORMATION: T7 polymerase promoter

<400> SEQUENCE: 2
aattctaata cgactcacta taggg                                          25

<210> SEQ ID NO 3
<211> LENGTH: 29
<212> TYPE: DNA
<213> ORGANISM: Artificial
<220> FEATURE:
<223> OTHER INFORMATION: HIV ref p1 (without T7 sequences shown)

<400> SEQUENCE: 3
cctgctatgt cacttcccct tggttctct                                      29

<210> SEQ ID NO 4
<211> LENGTH: 29
<212> TYPE: DNA
<213> ORGANISM: Artificial
<220> FEATURE:
<223> OTHER INFORMATION: HIV type F p1 (without T7 sequences shown)

<400> SEQUENCE: 4
ccagctatat cacttcccct aggttccct                                      29

<210> SEQ ID NO 5
<211> LENGTH: 20
<212> TYPE: DNA
<213> ORGANISM: Artificial
<220> FEATURE:
```

<223> OTHER INFORMATION: HIV ref p1 Short 1 (without T7 sequences shown)

<400> SEQUENCE: 5
cctgctatgt cacttcccct                                              20

<210> SEQ ID NO 6
<211> LENGTH: 20
<212> TYPE: DNA
<213> ORGANISM: Artificial
<220> FEATURE:
<223> OTHER INFORMATION: HIV ref p1 Short 2 (without T7 sequences shown)

<400> SEQUENCE: 6
tcacttcccc ttggttctct                                              20

<210> SEQ ID NO 7
<211> LENGTH: 29
<212> TYPE: DNA
<213> ORGANISM: Artificial
<220> FEATURE:
<223> OTHER INFORMATION: HIV ref p2

<400> SEQUENCE: 7
agtgggggga catcaagcag ccatgcaaa                                    29

<210> SEQ ID NO 8
<211> LENGTH: 36
<212> TYPE: DNA
<213> ORGANISM: Artificial
<220> FEATURE:
<223> OTHER INFORMATION: HIV WT MB (Me8)
<220> FEATURE:
<221> NAME/KEY: misc_feature
<222> LOCATION: (19)..(19)
<223> OTHER INFORMATION: n is inosine
<220> FEATURE:
<221> NAME/KEY: misc_feature
<222> LOCATION: (28)..(28)
<223> OTHER INFORMATION: n is inosine

<400> SEQUENCE: 8
ctatcccatc aatgaggang ctgcagantg ggatag                            36

<210> SEQ ID NO 9
<211> LENGTH: 43
<212> TYPE: DNA
<213> ORGANISM: Artificial
<220> FEATURE:
<223> OTHER INFORMATION: Entero ref p1

<400> SEQUENCE: 9
aattctaata cgactcacta tagggcaccg gatggccaat cca                    43

<210> SEQ ID NO 10
<211> LENGTH: 40
<212> TYPE: DNA
<213> ORGANISM: Artificial
<220> FEATURE:
<223> OTHER INFORMATION: Entero ref p2

<400> SEQUENCE: 10
gatgcaaggt cgcatatgag ggtgtgaaga gcctattgag                        40

<210> SEQ ID NO 11
<211> LENGTH: 34
<212> TYPE: DNA
<213> ORGANISM: Artificial

```
<220> FEATURE:
<223> OTHER INFORMATION: Entero WT MB

<400> SEQUENCE: 11
ccatgcgtcc tccggcccct gaatgcgcgc atgg                            34

<210> SEQ ID NO 12
<211> LENGTH: 32
<212> TYPE: DNA
<213> ORGANISM: Artificial
<220> FEATURE:
<223> OTHER INFORMATION: Entero IC Beacon

<400> SEQUENCE: 12
cgatgcgcaa agtatcatcc ctccaggcat cg                              32

<210> SEQ ID NO 13
<211> LENGTH: 48
<212> TYPE: DNA
<213> ORGANISM: Artificial
<220> FEATURE:
<223> OTHER INFORMATION: HSV ref p1

<400> SEQUENCE: 13
aattctaata cgactcacta tagggagacc agggccctgg aggtgcgg             48

<210> SEQ ID NO 14
<211> LENGTH: 20
<212> TYPE: DNA
<213> ORGANISM: Artificial
<220> FEATURE:
<223> OTHER INFORMATION: HSV ref p2

<400> SEQUENCE: 14
acgttcacca agctgctgct                                            20

<210> SEQ ID NO 15
<211> LENGTH: 35
<212> TYPE: DNA
<213> ORGANISM: Artificial
<220> FEATURE:
<223> OTHER INFORMATION: HSV WT MB (gen WT3)

<400> SEQUENCE: 15
cgatcggaaa aagtacatcg gcgtcatctc gatcg                           35

<210> SEQ ID NO 16
<211> LENGTH: 54
<212> TYPE: DNA
<213> ORGANISM: Artificial
<220> FEATURE:
<223> OTHER INFORMATION: Blocked P1 primer from Fig. 1

<400> SEQUENCE: 16
aattctaata cgactcacta tagggagaag gaggccagta acggcactct ctgc      54

<210> SEQ ID NO 17
<211> LENGTH: 39
<212> TYPE: DNA
<213> ORGANISM: Artificial
<220> FEATURE:
<223> OTHER INFORMATION: Target RNA sequence from Fig. 1

<400> SEQUENCE: 17
gcagagagtg ccgtaactgg tctctctgca gatcatgta                       39
```

```
<210> SEQ ID NO 18
<211> LENGTH: 10
<212> TYPE: DNA
<213> ORGANISM: Artificial
<220> FEATURE:
<223> OTHER INFORMATION: Target RNA sequence following RNase H treatment
      from Fig. 1

<400> SEQUENCE: 18
gcagagagtg                                                                 10

<210> SEQ ID NO 19
<211> LENGTH: 54
<212> TYPE: DNA
<213> ORGANISM: Artificial
<220> FEATURE:
<223> OTHER INFORMATION: Target RNA sequence following AMV-RT extension

<400> SEQUENCE: 19
gcagagagtg ccgtaactgg tctccttctc cctatagtga gtcgtattag aatt               54
```

MULTIPLEX NUCLEIC ACID AMPLIFICATION USING BLOCKED PRIMERS

STATEMENT OF PRIORITY

This application is a 35 U.S.C. §371 national phase application of PCT Application Serial No. PCT/EP2007/009715, filed Nov. 7, 2007, which claims priority to European Application No. 06023431.7, filed Nov. 10, 2006, the entire contents of each of which are incorporated by reference herein.

FIELD OF THE INVENTION

The present invention relates to in vitro amplification of nucleic acid sequences, and in particular to transcription-based amplification, providing improvements thereof. Specifically, the present invention provides methods that improve transcription-based amplification reactions when reagents for more than one amplification target are present, e.g., multiplex amplification reactions.

BACKGROUND OF THE INVENTION

Nucleic acid amplification has proven useful in numerous clinical applications including the detection and/or diagnosis of infectious diseases and pathological genomic abnormalities as well as nucleic acid polymorphisms that may not be associated with any pathological state. Nucleic acid amplification is particularly useful in circumstances where the quantity of the targeted nucleic acid is relatively small compared to other nucleic acids present in a sample, where only a small amount of the targeted nucleic acid is available, where the detection technique has low sensitivity, or where more rapid detection is desirable. For example, infectious agents may be accurately identified by detection of specific characteristic nucleic acid sequences. Because a relatively small number of pathogenic organisms may be present in a sample, the nucleic acid extracted from these organisms typically constitutes only a very small fraction of the total nucleic acid in the sample. Specific amplification of the characteristic nucleic acid sequences, if present, greatly enhances the sensitivity and specificity of the detection and discrimination processes.

Generally, the currently known amplification schemes can be broadly grouped into two classes based on whether the enzymatic amplification reactions are driven by continuous cycling of the temperature between the denaturation temperature, the primer annealing temperature, and the amplicon (product of enzymatic amplification of nucleic acid) synthesis temperature (thermocycling amplification), or whether the temperature is kept constant throughout the enzymatic amplification process (isothermal amplification). Typical cycling nucleic acid amplification technologies (thermocycling) are polymerase chain reaction (PCR), and ligase chain reaction (LCR). FSpecific protocols for such reactions are discussed in, for example, Short Protocols in Molecular Biology, 2nd Edition, A Compendium of Methods from Current Protocols in Molecular Biology, (Eds. Ausubel et al., John Wiley & Sons, New York, 1992) chapter 15. Reactions which are isothermal include: transcription-mediated amplification (TMA), nucleic acid sequence-based amplification (NASBA), and strand displacement amplification (SDA), among others.

Isothermal target amplification methods include transcription-based amplification methods, in which an RNA polymerase promoter sequence is incorporated into primer extension products at an early stage of the amplification (WO 89/01050), and further target sequence, or target complementary sequence, is amplified by transcription steps and digestion of an RNA strand in a DNA/RNA hybrid intermediate product. See, for example, U.S. Pat. Nos. 5,169,766 and 4,786,600. These methods include transcription mediated amplification (TMA), self-sustained sequence replication (3SR), Nucleic Acid Sequence Based Amplification (NASBA), and variations there of. See, for example, Guatelli et al. Proc. Natl. Acad. Sci. U.S.A. 87:1874-1878 (1990); U.S. Pat. Nos. 5,766,849 5,399,491; 5,480,784; 5,766,849; and 5,654,142 (TMA); U.S. Pat. No. 5,130,238 (Malek et al.); U.S. Pat. No. 5,409,818 and EP0329822 (Davey et al.); U.S. Pat. No. 5,654,142 (Kievits); and U.S. Pat. No. 6,312,928 (Van Gemen et al.) (nucleic acid sequence-based amplification (NASBA) techniques); and Kwoh et al., 1989, Proc. Natl. Acad. Sci. USA 86:1173-1177; Guatelli et al., 1990, Proc. Natl. Acad. Sci. USA 87:1874-1878; PCT Patent Publication No. WO 92/08800) (3SR). U.S. Pat. No. 5,744,311 (Fraiser); U.S. Pat. No. 5,648,211 (Fraiser); U.S. Pat. No. 5,455,166 (Walker) and U.S. Pat. No. 5,631,147 (Lohman), describe isothermal amplification systems based on strand displacement amplification (SDA).

DNA NASBA methods (DNA target amplification resulting in RNA amplicons) have also been described ((see, e.g., 'Method for the amplification and detection of DNA using transcription based amplification' (WO 02/070735), 'Method for the amplification and detection of HBV DNA using transcription based amplification' (WO 02/072881) and 'Nucleic acid sequences that can be used as primers and probes in the amplification and detection of HSV DNA and method for the amplification and detection of HSV DNA using transcription based amplification' (EP04078166.8)).

U.S. Pat. Nos. 4,683,195 and 4,683,202 provide description of PCR. U.S. Pat. No. 5,792,607 (Backman) describes amplification methods referred to as ligase chain reactions (LCR; see also Wu and Wallace, 1989, Genomics 4:560-569 and Barany, 1991, Proc. Natl. Acad. Sci. USA 88:189-193). Other approaches include Polymerase Ligase Chain Reaction (Barany, 1991, PCR Methods and Applic. 1:5-16); Gap-LCR (PCT Patent Publication No. WO 90/01069); Repair Chain Reaction (European Patent Publication No. 439,182 A2); Q-beta replicase, transcription mediated iso CR cycling probe technology, and cascade rolling circle amplification (CRCA). Additional U.S. patent documents which describe nucleic acid amplification include U.S. Pat. Nos. 4,876,187; 5,030,557; 5,399,491; 5,485,184; 5,554,517; 5,437,990; 5,399,491, 5,554,516 and 6,551,778. A survey of amplification systems is provided in Abramson and Myers, 1993, Current Opinion in Biotechnology 4:41-47.

In a standard NASBA reaction, large amounts of single stranded RNA are generated from either single stranded RNA (ssRNA) or DNA (ssDNA) or double stranded DNA (ds-DNA) (U.S. Pat. No. 5,654,142). When RNA is to be amplified with NASBA the ssRNA serves as a template for the synthesis of a first DNA strand by elongation of a first primer containing a RNA polymerase recognition site. This DNA strand in turn serves as the template for the synthesis of a second, complementary, DNA strand by elongation of a second primer, resulting in a double stranded active RNA-polymerase promoter site, and the second DNA strand serves as a template for the synthesis of large amounts of the first template, the ssRNA, with the aid of a RNA polymerase (U.S. Pat. No. 5,409,818).

Transcription based amplification techniques involve the transcription of multiple RNA copies from a template comprising a promoter recognized by an RNA polymerase. With these methods multiple RNA copies are transcribed from a DNA template that comprises a functional promoter recognized by the RNA polymerase. These copies are used as a target again from which a new amount of the DNA template is obtained etc. Isothermal transcription based amplification can be performed (Davey et al., EP 323822 (NASBA); Gingeras et al., EP0373960; Kacian et al., EP0408295), and also transcription based amplification reactions may be performed with thermostable enzymes which allow the reaction to be carried out at more elevated temperatures (e.g., EP0682121, Toyo Boseki K K).

The methods as described in EP0323822, EP0373960 and EP0408295 are isothermal continuous methods. With these methods four enzyme activities are required to achieve amplification: an RNA dependent DNA polymerase activity, an DNA dependent DNA polymerase activity, an RNase (H) activity and an RNA polymerase activity. Some of these activities can be combined in one enzyme, so usually only two or three enzymes are necessary. Enzymes having RNA dependent DNA polymerase activities are enzymes that synthesize DNA from an RNA template. A DNA dependent DNA polymerase thus synthesizes DNA from a DNA template. In transcription-based amplification reactions a reverse transcriptase such as AMV (Avian Myoblastosis Virus) or MMLV (Moloney Murine Leukemia Virus) reverse transcriptase may be used. Such enzymes have both RNA- and DNA dependent DNA polymerase activity but also an inherent RNase activity. In addition an RNase may be added to the reaction mixture of a transcription based amplification reaction, such as *E. coli* RNase H.

Conventional techniques of molecular biology and nucleic acid chemistry, which are within the skill in the art, are fully explained in the literature. See, for example, Sambrook et al., 1989, Molecular Cloning—A Laboratory Manual, Cold Spring Harbor Laboratory, Cold Spring Harbor, N.Y.; Oligonucleotide Synthesis (M. J. Gait, ed., 1984); Nucleic Acid Hybridization (B. D. Hames and S. J. Higgins. eds., 1984); and a series, Methods in Enzymology (Academic Press, Inc.). Nucleic acid hybridization techniques have been described for example, in Sambrook et al.; U.S. Pat. No. 4,563,419 (Ranki) and U.S. Pat. No. 4,851,330 (Kohne) and in Dunn et al., *Cell* 12, pp. 23-26 (1978) among many other publications.

Detection methods utilizing nucleic acids are also known. Nucleic acids are often labeled for various detection purposes. For example, methods described in U.S. Pat. No. 4,486,539 (Kourlisky); U.S. Pat. No. 4,411,955 (Ward); U.S. Pat. No. 4,882,269 (Schneider) and U.S. Pat. No. 4,213,893 (Carrico), illustrate preparation of labeled detection probes for detecting specific nucleic acid sequences. Furthermore, before or after exposing an extracted nucleic acid to a probe, the target nucleic acid can be immobilized by target-capture means, either directly or indirectly, using a "capture probe" bound to a substrate, such as a bead or a magnetic bead. Examples of target-capture methodologies are described by Ranki et al., U.S. Pat. No. 4,486,539, and Stabinsky, U.S. Pat. No. 4,751,177. Further uses of probes have been described, for example, in U.S. Pat. Nos. 5,210,015; 5,487,972; 5,804,375; 5,994,076.

Additionally, a class of oligonucleotide probes, referred to as molecular beacons, that facilitate homogeneous detection of specific nucleic acid target sequences has been described (Piatek et al. (1998) Nature Biotechnology 16:359-363; Tyagi and Kramer (1996) Nature Biotechnology 14:303-308). Molecular beacons are nucleic acid sequences that contain a fluorophore and a quencher. By design, molecular beacons are expected to fold into stem-loop structures in which the fluorophore is placed in close proximity to the quencher. When the molecular beacon is illuminated with light corresponding to the excitation wavelength of the fluorescent group, no fluorescence is observed, because energy transfer occurs between the fluorescent group and the quenching group, such that light emitted from the fluorescent group upon excitation is absorbed by the quenching group. The loop region of molecular beacons is designed to contain a nucleotide sequence complementary to the target sequence of interest. When the molecular beacon is contacted with sequences complementary to the loop, the loop hybridizes to this sequence. This process is energetically favored as the intermolecular duplex formed is longer, and therefore more stable, than the intramolecular duplex formed in the stem region. As this intermolecular double helix forms, torsional forces are generated that cause the stem region to unwind. As a result, the fluorescent group and the quenching group become spatially separated such that the quenching group is no longer able to efficiently absorb light emitted from the fluorescent group. Thus, binding of the molecular beacon to its target nucleic acid sequence is accompanied by an increase in fluorescence emission from the fluorescent group. Molecular beacons undergo intermolecular hybridization upon interaction with the specific target sequence. Molecular beacons have been used for homogeneous detection of specific nucleic acid sequences, both DNA and RNA (Leone et al. (1998) Nucleic Acids Research 26:2150-2155; Piatek et al. (1998); Tyagi and Kramer (1996)).

A number of target nucleic acids have proven difficult to amplify to readily detectable levels and/or with appropriate specificity (e.g., HCV (Pavio and Lai, J. Biosci. 28(3): 287-304 (2003)), among others), and methods to improve amplification are thus needed. Additionally, improvements to amplification can be useful to any target for which faster results are desired. Furthermore, some targets have proven difficult to amplify when in a multiplex reaction with other targets and/or primers and probes specific for other targets.

Some improvements in amplification have been made. U.S. Pat. No. 6,338,954 (van Gemen) discloses a method for non-specific amplification. U.S. Pat. No. 6,509,157 discloses amplification primers used in PCR reversibly blocked such that primer is unblocked at temperatures used to start PCR. U.S. Pat. No. 5,849,497 discloses a method for inhibition of amplification of at least one target sequence in a PCR reaction.

Thus, while many advances have been made in the area of amplification of nucleic acids, there is still a need to improve the product yield, to achieve improved sensitivity for a specific target and thus to provide more useful assays, particularly when reagents specific for more than one target are present, such as in a multiplex assay, and even more particularly, when amplification of one target in a multiplex assay dominates over amplification of a second target in the assay. The present invention provides methods to improve transcription-based amplification of a specific target that can be applied to many selected target nucleic acids and combinations thereof.

SUMMARY OF THE INVENTION

The present invention provides a method of performing a specific transcription-based amplification reaction of a selected first target nucleic acid in a sample, in a reaction wherein reagents specific for amplification of more than one target nucleic acid are present, comprising
(1) contacting the sample with
(a) a first promoter oligonucleotide having a 5' end and a 3' end, the first promoter oligonucleotide comprising, at the 5' end, an RNA polymerase promoter sequence, and, 3' of the RNA polymerase promoter sequence, a sequence complementary to a first target portion of the first target nucleic acid, and (b) a second promoter oligonucleotide having a 5' end and a 3' end, the second promoter oligonucleotide comprising, at the 5' end, an RNA polymerase promoter sequence, and, 3' of the RNA polymerase promoter sequence, a sequence complementary to a first target portion of a second target nucleic acid wherein further, the second promoter oligonucleotide comprises, at the 3' end, a blocking moiety such that extension therefrom is essentially prohibited, and (2) providing selected reagents and conditions for transcription-based amplification.

The present invention further provides a method of performing a specific transcription-based amplification reaction of a selected first target nucleic acid in a sample, in a reaction wherein more than one target nucleic acid, if present in the sample, is to be amplified, comprising (1) contacting the sample with (a) a first promoter oligonucleotide having a 5' end and a 3' end, the first promoter oligonucleotide comprising, at the 5'end, an RNA polymerase promoter sequence, and, 3' of the RNA polymerase promoter sequence, a sequence complementary to a first target portion of the first target nucleic acid, and (b) a second promoter oligonucleotide having a 5' end and a 3' end, the second promoter oligonucleotide comprising, at the 5'end, an RNA polymerase promoter sequence, and, 3' of the RNA polymerase promoter sequence, a sequence complementary to a first target portion of a second target nucleic acid wherein further, the second oligonucleotide comprises, at the 3' end, a blocking moiety such that extension therefrom is prohibited, and (2) providing selected reagents and conditions for transcription-based amplification.

The present invention additionally provides a composition for performing multiplex hybridization to and amplification of two or more target nucleic acids comprising two or more promoter oligonucleotides, each having a 5' end and a 3' end, a first promoter oligonucleotide comprising, at the 5'end, an RNA polymerase promoter sequence, and, 3' of the RNA polymerase promoter sequence, a sequence complementary to a first target portion of the first target nucleic acid, and a second promoter oligonucleotide having a 5' end and a 3' end, the second promoter oligonucleotide comprising, at the 5'end, an RNA polymerase promoter sequence, and, 3' of the RNA polymerase promoter sequence, a sequence complementary to a first target portion of a second target nucleic acid wherein further, the second promoter oligonucleotide comprises, at the 3' end, a blocking moiety such that extension therefrom is essentially prohibited.

BRIEF DESCRIPTION OF THE DRAWINGS

FIG. 5 shows HIV NASBA amplification in presence of Entero unblocked primers. An input of 50 IU WRS of HIV-1 subtype B (five samples) was used as input. A sample without template (NT) was used as negative control. The amplifications were performed in presence of both the Entero primers, a 3' DabSyl blocked HIV ref p1 primer, a HIV ref p2 primer and a HIV specific molecular beacon (HIV WT MB, Table 1).

DETAILED DESCRIPTION OF THE INVENTION

Figure 1:
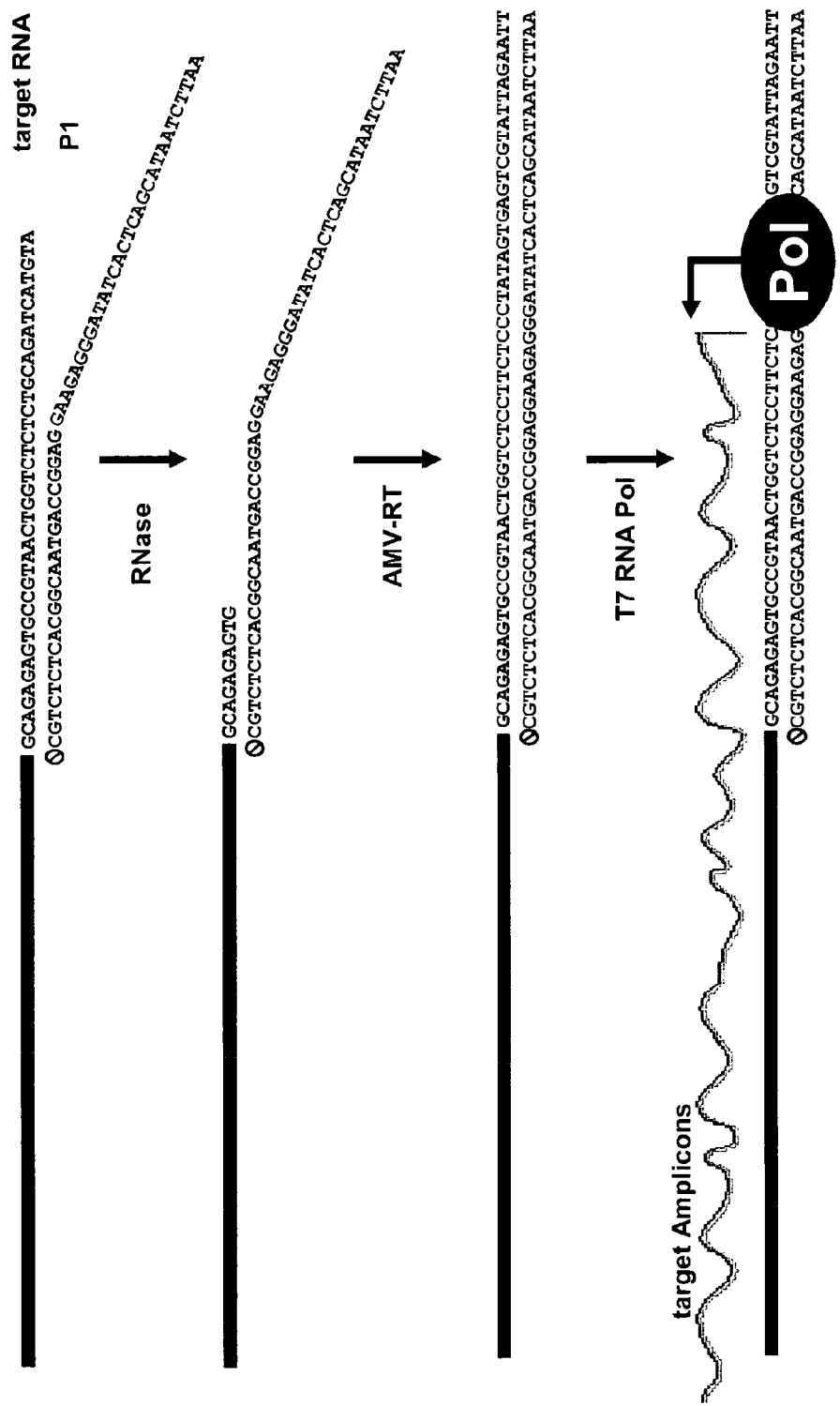
FIG. 1 shows a proposed mechanism for NASBA with blocked P1 primer. Target RNA in top sequence is the nucleotide sequence of SEQ ID NO:17. The blocked primer P1 is the complement of the nucleotide sequence of SEQ ID NO:19 and is shown hybridized to the nucleotide sequence of SEQ ID NO:17 (in part) in the first step of the assay, to the nucleotide sequence of SEQ ID NO:18 (in part) in the second step of the assay and to the nucleotide sequence of SEQ ID NO:19 in the third and fourth steps of the assay.

In general, the present invention relates to a method for increasing the performance of amplification reactions, more specifically, by the use in an amplification reaction, of primers, specific for a selected target, wherein one or more is blocked at its 3' end, namely by addition of a blocking moiety, in transcription based amplification assays such as NASBA, TMA and 3SR. The blocked primer is non-extendable and is specific for the target (i.e., it is not for use with non-specific oligo-dT primers). Additionally, in the amplification reaction, a second, typically non-blocked, reverse-strand target-specific primer (often referred to as "P2") is utilized to provide high amplification levels. The blocked primer is the P1 (i.e., T7 Pol-site-containing) primer. The blocked primer, in transcription-based amplification reactions, blocks reverse transcriptase-mediated extension of P1, and possibly provides an alternative start of these reactions.

Transcription based amplification techniques involve the transcription of multiple RNA copies from a template comprising a promoter recognized by an RNA polymerase. Transcription based amplification techniques have also been adapted to function with DNA as the input nucleic acid, typically utilizing selected restriction endonucleases to generate a starting template (see, e.g., Example 3). Isothermal transcription based amplification can be performed or transcription based amplification reactions may be performed with thermostable enzymes (and corresponding thermostable polymerase promoter sequences utilized in the promoter-primer). Standard isothermal transcription based amplifications are usually carried out at a temperature around 41° C. while thermostable enzymes allow the reaction to be carried out at more elevated temperatures (e.g., 50-70° C.) (e.g., EP0682121, Toyo Boseki K K).

In an isothermal continuous method, four enzyme activities are required to achieve amplification: an RNA dependent DNA polymerase activity, a DNA dependent DNA polymerase activity, an RNase (H) activity and an RNA polymerase activity. In a preferred embodiment, some of these activities can be combined in one enzyme, so that only 2 or 3 enzymes are necessary. In transcription-based amplification reactions, a reverse transcriptase such as AMV (Avian Myoblastosis Virus) or MMLV (Moloney Murine Leukemia Virus) reverse transcriptase may be used. Such enzymes have both RNA- and DNA dependent DNA polymerase activity but also an inherent RNase activity. In addition, an RNase may be added to the reaction mixture of a transcription based amplification reaction, such as E. coli RNase H.

DNA dependent RNA polymerases synthesize multiple RNA copies from a DNA template including a promoter recognized by the RNA polymerase. Examples of RNA polymerases are polymerases from E. coli and bacteriophages T7, T3 and SP6. An example of an RNA polymerase commonly used with transcription based amplification methods is T7 polymerase. Thus, in a preferred embodiment of the invention, the promoter that is incorporated into the template used for transcribing multiple copies of RNA would be the T7-promoter. The amplification reaction of the present invention can be started by bringing together the sample, the appropriate enzymes that together provide the above-mentioned activities, a P1 promoter (optionally blocked at its 3' end) and corresponding P2 primer, each specific for a first target, and a (typically) 3'-blocked P1 primer and corresponding P2 primer, each specific for a second target, at the appropriate temperature for NASBA (or other chosen amplification reaction), depending on whether the enzymes are thermostable or not, and with standard buffers.

Transcription based amplification methods are particularly useful if the input material is single stranded RNA, although single or double stranded DNA can likewise be used as input material. Focusing first on any single amplification that can occur within a multiplex amplification, when a transcription based amplification method is practiced on a sample with single stranded RNA (of the "plus" sense) comprising a target sequence to be amplified (such target sequence having a 3' end (the "first target portion") and a 5' end (the "second target portion")), a pair of oligonucleotides that is conveniently used would comprise or consist essentially of:

a first oligonucleotide (herein typically referred to as a "P1 primer") that is capable of hybridizing (at appropriately stringent conditions to achieve the desired specificity of hybridization) to the 3' end of the target sequence by incorporating a sequence complementary (as defined herein) to a first target portion of the target nucleic acid (the hybridizing part of a P1 primer oligonucleotide has the opposite polarity as the plus RNA used as input material), which oligonucleotide additionally has the sequence of a polymerase promoter (if utilizing T7 polymerase in the amplification, then preferably this is the T7 polymerase promoter) attached to its 5' end and, optionally, a blocking moiety attached to its 3' end. By "RNA polymerase promoter sequence" or "having the sequence of an RNA polymerase promoter" when describing a single-stranded oligonucleotide is meant a sequence that, when double stranded, can function as an RNA polymerase promoter. Reagents can also include a second oligonucleotide ("P2 primer") which comprises or consists essentially of a portion of the 5' end of the target sequence (the "second target portion") (a P2 primer oligonucleotide has the same polarity as the plus RNA). The second (P2) oligonucleotide comprises or consists essentially of a sequence having sufficient homology to the second target portion to achieve hybridization to a nucleic acid fully complementary to it, at appropriately stringent conditions to achieve the desired specificity of hybridization. Each primer is capable of supporting primer extension, under standard conditions, when not blocked.

In a multiplex amplification, reagents for amplification of a second (or more) target nucleic acid(s) are also present and one or more of the P1 primers is blocked at its 3' end. Such reagents can include a second promoter oligonucleotide (second P1 primer) having a 5' end and a 3' end, the second promoter oligonucleotide comprising, at the 5'end, an RNA polymerase promoter sequence (preferably functional with the same polymerase as the promoter of the first promoter oligonucleotide), and, 3' of the RNA polymerase promoter sequence, a sequence complementary to a first target portion of a second target nucleic acid wherein further, the second promoter oligonucleotide optionally comprises, at the 3' end, a blocking moiety such that extension therefrom is essentially prohibited. These reagents also can include a second primer oligonucleotide (second P2 primer) comprising a sequence homologous to a second target portion of the second target nucleic acid, which second target portion is 5' of the first target portion of the second target nucleic acid.

When two or more sets of amplification oligonucleotides (typically one P1 primer and one P2 primer for each selected target nucleic acid; at least one, but alternatively, two, three or more (possibly all P1 primers in the reaction, or at least one P1 primer per nucleic acid present in the reaction) of the P1 primers can be blocked at its 3' end), together with all enzymes having the appropriate activities for the selected amplification method, and a sufficient supply of the necessary ribonucleotides and deoxy-ribonucleotides are put together in one reaction mixture and are kept under the appropriate amplification conditions (for example, under the appropriate buffer conditions and at the appropriate temperature, all known in the art) for a sufficient period of time, an isothermal continuous amplification reaction will start. All steps of this process can take place at the same time since all reagents are present in the reaction vessel.

The present invention further provides a means for increasing the specificity of a transcription-based amplification reaction. In particular, use of one or more blocked primers "P1" of the invention may be used as a general tool to increase the specificity of one or more individual NASBA amplifications within a multiplex amplification as described and exemplified herein. Thus, it is to be noted that, in certain multiplex reactions, a "target" nucleic acid can be a nucleic acid whose amplification is modified (e.g. decreased) by use of a 3' blocked primer, often to allow improved or increased amplification of another "target" nucleic acid.

Thus the present invention provides a method of performing a specific transcription-based amplification reaction of a selected first target nucleic acid in a sample, in a reaction wherein reagents specific for amplification of more than one target nucleic acid are present, comprising (1) contacting the sample with (a) a first promoter oligonucleotide having a 5' end and a 3' end, the first promoter oligonucleotide comprising, at the 5'end, an RNA polymerase promoter sequence, and, 3' of the RNA polymerase promoter sequence, a sequence complementary to a first target portion of the first target nucleic acid, and (b) a second promoter oligonucleotide having a 5' end and a 3' end, the second promoter oligonucleotide comprising, at the 5'end, an RNA polymerase promoter sequence, and, 3' of the RNA polymerase promoter sequence, a sequence complementary to a first target portion of a second target nucleic acid wherein further, the second promoter oligonucleotide comprises, at the 3' end, a blocking moiety such that extension therefrom is essentially prohibited, and (2) providing selected reagents and conditions for transcription-based amplification. Either the first promoter oligonucleotide or the second promoter oligonucleotide, or both, can be blocked at the 3' end by a blocking moiety. The selected reagents can comprise a first primer oligonucleotide comprising a sequence homologous to a second target portion of the first target nucleic acid, which second target portion is 5' of the first target portion of the first target nucleic acid and a second primer oligonucleotide comprising a sequence homologous to a second target portion of the second target nucleic acid, which second target portion is 5' of the first target portion of the second target nucleic acid. The sample can further be contacted with a detectably labeled first probe oligonucleotide homologous to a third target portion of the first target nucleic acid, which third target portion is located between the first and second target portions, and, if desired, a detectably labeled second probe oligonucleotide homologous to a third target portion of the second target nucleic acid, which third target portion is located between the first and second target portions.

The present method is useful for multiple targets, e.g., two, three, four, five, six or more targets in a single multiplex reaction. Thus, the method can further comprise contacting the sample with a third (fourth, fifth, sixth, etc.) promoter oligonucleotide having a 5' end and a 3' end, the third promoter oligonucleotide comprising, at the 5'end, an RNA polymerase promoter sequence, and, 3' of the RNA polymerase promoter sequence, a sequence complementary to a first target portion of a third target nucleic acid. Accordingly, a third (fourth, fifth, sixth, etc.) P2 primer can also be included.

The target nucleic acid is a specific, selected nucleic acid of known sequence, to which the P1 primer ("promoter oligonucleotide") and P2 primer ("primer oligonucleotide") is designed to hybridize specifically, i.e., under hybridization conditions sufficiently stringent to achieve the desired specificity, which will depend upon the goal of the reaction (see, e.g. Sambrook, et al). In some uses, for example to distinguish one strain of organism from another, the sequences of the primers and amplification reaction can be designed such that the P1 primer and/or P2 primer binds only to an exact complement. In other uses, for example to ensure detection of any strain of an organism present in a sample, a primer set and amplification reaction can be designed so as to hybridize and amplify the nucleic acid of many or all strains of a target organism. Thus, the target nucleic acids in a reaction can be nucleic acids each of different strains of the same organism. Alternatively, the target nucleic acids can be nucleic acids of different organisms.

Regardless of specificity selected, the present method can be utilized to enhance amplification of one or more of the target nucleic acids, again depending upon the design and goal of the amplification. Additionally, it is noted that a target nucleic acid is not a polyA region of an mRNA, since a primer designed to bind to a polyA region would bind essentially any polyA RNA, not specifically and/or selectively, the target RNA(s).

The present invention further provides a composition comprising two or more promoter oligonucleotides (at least a first and a second promoter oligonucleotide), each having a 5' end and a 3' end, for performing multiplex hybridization to and amplification of two or more target nucleic acids, a first promoter oligonucleotide comprising, at the 5'end, an RNA polymerase promoter sequence, and, 3' of the RNA polymerase promoter sequence, a sequence complementary to a first target portion of the first target nucleic acid, and a second promoter oligonucleotide having a 5' end and a 3' end, the second promoter oligonucleotide comprising, at the 5'end, an RNA polymerase promoter sequence, and, 3' of the RNA polymerase promoter sequence, a sequence complementary to a first target portion of a second target nucleic acid wherein further, the second promoter oligonucleotide comprises, at the 3' end, a blocking moiety such that extension therefrom is essentially prohibited.

The present invention further provides a composition comprising two or more promoter oligonucleotides for performing multiplex hybridization to and amplification of two or more target nucleic acids, a first promoter oligonucleotide comprising (1) a hybridization region comprising a nucleotide sequence complementary to a first target portion of a first target nucleic acid and having a 5' end and a 3' end, (2) a promoter region 5' of the hybridization region comprising a sequence that, when double stranded, can function as an RNA polymerase promoter, and (3) a blocking moiety attached to the 3' end of the hybridization region; and a second promoter oligonucleotide comprising (1) a hybridization region comprising a nucleotide sequence homologous to a first target portion of a second target nucleic acid and having a 5' end and a 3' end, (2) a promoter region 5' of the hybridization region comprising a sequence that, when double stranded, can function as an RNA polymerase promoter, and (3) a blocking moiety attached to the 3' end of the hybridization region. The composition can comprise two or more promoter oligonucleotides wherein the first promoter oligonucleotide can consist essentially of, or consist of (1) a hybridization region comprising a nucleotide sequence complementary to a first target portion of a first target nucleic acid and having a 5' end and a 3' end, (2) a promoter region 5' of the hybridization region comprising a sequence that, when double stranded, can function as an RNA polymerase promoter, and (3) a blocking moiety attached to the 3' end of the hybridization region; and wherein the second promoter oligonucleotide can consist essentially of, or consist of (1) a hybridization region comprising a nucleotide sequence homologous to a first target portion of a second target nucleic acid and having a 5' end and a 3' end, (2) a promoter region 5' of the hybridization region comprising a sequence that, when double stranded, can function as an RNA polymerase promoter, and (3) a blocking moiety attached to the 3' end of the hybridization region.

Figure 2:
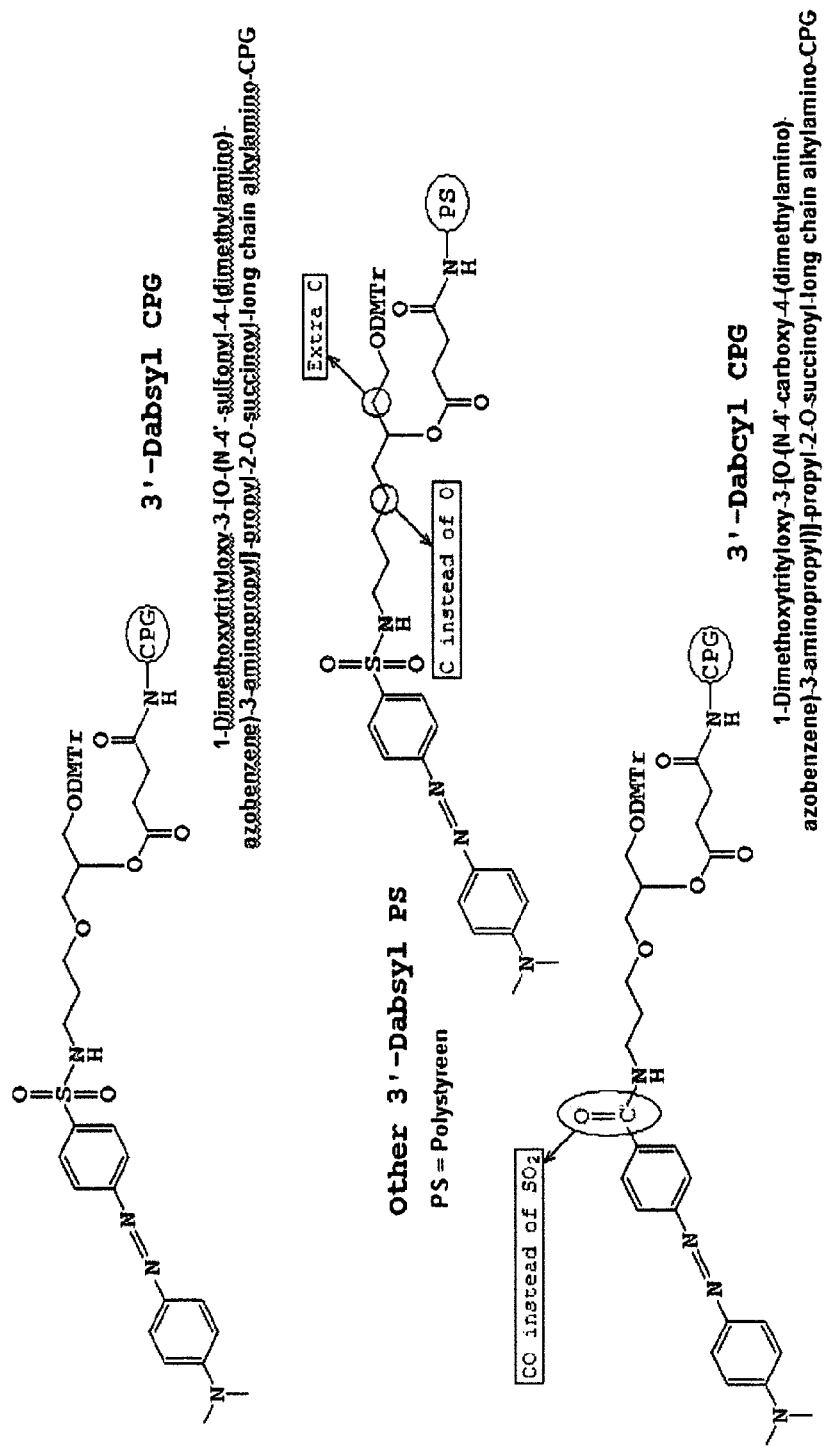
FIG. 2 shows the chemical structure of 3'-Dabsyl CPG, a variant 3'-Dabsyl PS (polystyreen) and 3'-Dabcyl CPG.

A blocking moiety useful in the invention is any blocking moiety that, when attached to the 3' end of an oligonucleotide primer, can essentially block the extension of the primer, when the primer is hybridized to a target in a transcription-based amplification reaction, by the appropriate enzyme (e.g., reverse transcriptase) but yet allow for improved production of RNA copies by RNA polymerase in the NASBA reaction as compared to the same NASBA reaction with a non-blocked version of the primer. The blocking moiety is particularly useful when attached to the P1 (promoter-containing) primer of a transcription-based amplification reaction. Blocking moieties can preferably be dabsyl (see FIG. 2). Additionally, dabcyl (same basic chemical structure as dabsyl, with a substitution of —CO— in place of —$SO_2$—) can be utilized as a blocking moiety. Dabsyl has a sulfur substituted for a carbon but the attachment chemistry is the same for both dabsyl and dabcyl (See Examples). Dabsyl and dabcyl each provide efficient purification of blocked primers from unblocked primers. Additionally, the blocking moiety can be an amino group, —$NH_2$. The blocking moiety can be phosphate, —$PO_4$. Dabsyl blocking moieties can be attached to the 3' end of an oligonucleotide primer during automated DNA synthesis using a dabsylated 3'-controlled pore glass (CPG) support. (3'-Dabsyl CPG: 1-Dimethoxytrityloxy-3-[O—(N-4'-sulfonyl-4-(dimethylamino)-azobenzene)-3-aminopropyl]-propyl-2-O-succinoyl-long chain alkylamino-CPG). Similarly, dabcyl and amino groups can be added during the first step of oligonucleotide synthesis. Methods of attachment of moieties that can be utilized as blocking moieties are known to persons of skill in the art. The attachment may be readily achieved by replacing the free hydroxyl at the 3' end of the primer with a blocking moiety. The blocking moiety can also be a noncomplementary (to the target) oligonucleotide, though for some applications, this may not be the preferable blocking moiety. In a preferred embodiment, one or both (or all, if more than two) of the blocking moieties remains present at the 3'end of the second promoter oligonucleotide at any selected NASBA amplification reaction temperature; in other words, it remains present on the primer throughout the transcription-based amplification. For any selected target and primer set, the preferred blocking moiety can readily be determined, utilizing the teachings herein, by a person of skill in the art.

By a blocking moiety "essentially" prohibiting or blocking extension from an oligonucleotide is meant that sufficient extension of the oligonucleotide by the appropriate enzyme is inhibited to improve amplification of the multiplex reaction measurably. In a preferred embodiment, the inhibition appears to be complete but also it is recognized that it is possible that in such a case a few or several extensions are in fact occurring. Furthermore, the invention contemplates that extension of a few or several molecules may be beneficial to the multiplex reaction, while the extension is still considered "essentially" prohibited.

Based upon the teachings herein, one of skill in the art can optimize, for any given multiplex reaction, the desired percentage of any or all of the reaction's primers having the blocking moiety attached. In general, it is preferred that a batch of any given primer utilized in an amplification reaction have a high percentage of primers having the moiety attached (in some instances within this application, this is referred to as high purity, as is clear by the context). Preferably at least 85%, more preferably, at least 86%, 87%, 88%, 89%, 90%, 91%, 92%, 93%, 94%, 95%, 96%, 97%, 98%, 99% or 100% of a particular blocked primer utilized in an amplification reaction will have the moiety attached. In general, any batch of synthesized primers having the blocking moiety attached as a first step of the synthesis should have a high percentage of primers having the moiety attached. Additional purification steps, such as HPLC and/or PAGE, can be performed, if desired. The purification by PAGE and/or HPLC can be utilized to vary the percentage of primer having the blocking moiety attached, as selected by the person of skill in the art. Further, one can select one primer in a multiplex reaction to have a higher purity, i.e., higher percentage of primers blocked, than the other, as desired and/or optimized for the particular targets, primers and reaction. A desired ratio of blocked: unblocked primers can be selected, based on optimization for any particular amplification result desired (e.g., 85:15, 90:10, 95:5, 99:1).

As used in the claims and in support thereof, the modifiers "a," "an," and "the" can mean singular or plural, unless the context dictates otherwise.

Starting material can be derived from any desired source, such as a sample from a human or other mammal (such as tissue, cells, blood, plasma, CSF, sputum, swabbings, etc.), an environmental sample, a product sample from a production or manufacturing line, etc. For example, starting material can include whole blood, blood serum, buffy coat, urine, feces, liquor cerebrospinales, sperm, saliva tissue, cell culture, foods products, vaccines, milk infected with a virus or a bacterium, vegetable material, gram-positive bacteria, yeast, mould, body fluid and biological material possibly infected with viruses or bacteria. Isolation of nucleic acid from such samples for use in amplification is well known in the art.

An oligonucleotide having promoter sequences recognized by an RNA polymerase (when double-stranded) in addition to a sequence for hybridization to a target is typically referred to herein as a "P1 primer". A particularly useful, and often used, RNA polymerase is T7 polymerase and the T7 polymerase promoter region. An oligonucleotide including T7 promoter sequences can be useful as a primer, and, when utilized as such, may herein be referred to as a "P1 primer", "P1-type primer" "promoter-oligonucleotide", or simply as "P1". In a transcription-based amplification reaction (e.g., NASBA, TMA), as is known in the art, these T7 promoter sequences have a function in the amplification reaction, priming the transcription of RNA from the target template once rendered double-stranded by earlier steps in the amplification reaction. The nucleotide sequences of primers exemplified herein as of the "P1" type are typically listed without the T7 promoter sequences, but in the experiments, such T7 promoter sequences are present. T7 promoter sequences that can be used include, but are not limited to the following: AATT-TAATACGACTCACTATAGGG (SEQ ID NO.: 1) and ATTCTAATACGACTCACTATAGGG (SEQ ID NO.: 2). The nucleic acid sequence of the T7 polymerase promoter is well-known to persons skilled in the art, and though a particular sequence is exemplified herein, functional equivalents having slight variations may be designed. As described herein, these sequences are utilized in the region of the P1 primer that is 5' to the region of target-specific sequence. Primers are readily synthesized to include these sequences by standard oligonucleotide synthesis techniques. Moreover, it is also in the scope of the invention to propose P1 primer, also called promoter oligonucleotide, having extra nucleotide stretch between the (RNA polymerase) promoter sequence and the sequence complementary to the target of interest. This extra nucleotide stretch is preferably constituted by 1-5 nucleotides in length, said nucleotides neither are part of the promoter sequence nor are complementary to said target. In a particularly interesting way of realization, the stretch is 2-3 nucleotides in length. Always in a particularly interesting way of realization, the stretch is mainly constituted by purine nucleotides (A and G).

In the specification, as well as in the claims, by "promoter oligonucleotide having a 5' end and a 3' end, the promoter oligonucleotide comprising, at the 5'end, an RNA polymerase promoter sequence, and, 3' of the RNA polymerase promoter sequence, a sequence complementary to a target portion of a target nucleic acid" "as used herein is meant that an extra nucleotide stretch, as defined above, can be present between the promoter sequence and the sequence complementary to the target of interest.

Hybridization is typically performed under stringent hybridization conditions. Stringent hybridization conditions are described in Sambrook, et. al, Molecular Cloning: A Laboratory Manual, 2nd Ed. Cold Spring Lab. Press, December 1989. However, hybridization conditions can be modified and selected to suit the particular reaction design, including the $T_m$s of the selected primers and the temperature at which the amplification reaction is to be performed. One of skill in the art can suitably design the appropriate reaction conditions for the selected type of amplification and for the selected combination of targets and primers.

"Complementary" can mean, depending on the context, exactly complementary to the target nucleic acid or sufficiently complementary to allow specific hybridization to the target nucleic acid under the selected hybridization conditions for the amplification reaction. Similarly, a sequence "homologous" to a target nucleic acid can mean that the sequence is of exact, or nearly exact, identity to the nucleic acid, such that it would specifically hybridize to a nucleic acid exactly complementary to the target nucleic acid. As used herein, stringent hybridization conditions are those conditions that provide selective hybridization for a selected target(s). By "selective hybridization" as used herein is meant that a nucleic acid can hybridize to a target nucleic acid under sufficient stringency conditions without significant hybridization to a nucleic acid likely to be present in the reaction but not of interest. Conditions can be selected to allow for detection of, for example, one or more related nucleic acids having, e.g., one, two, or three mismatches, as in, for example, related strains of the same organism, or they can be selected to provide that hybridization only occurs with one selected target, e.g., such that it differentiates between two strains, depending upon the purpose of the hybridization, amplification and detection. Such conditions selection is known to persons of skill in the art.

The target can be any selected nucleic acid, depending upon the amplification reaction to be performed. The specific target region chosen can be optimized by applying principles known to those of skill in the art. Once target sequences are selected, the P1 primer can be designed by including the T7 promoter sequence for use at the 5'end of the P1 primer, which T7 promoter sequence is linked directly or indirectly (in the latter case, a purine strech can be present in between T7 promoter and hybridizing sequence) to the 5' end of the selected sequence specific for the target. A blocking moiety is attached at the 3' end of the P1 primer. The sequences specific for the target are selected to be complementary to the target sequence, in particular, to be sufficiently complementary to allow hybridization of the primer to the target nucleic acid at the selected hybridization conditions. By use of the methods taught herein, specificity for the binding of the target-specific portion of the P1 primer can be customized. Preferred targets are those whose transcription-based amplification is improved by use of a 3'-blocked P1 primer as disclosed herein. In particular, targets for which the herein method are useful can be those which, when reagents for amplification of more than one target, are less preferentially amplified. The method can also be utilized to improve the overall amplification of all targets achieved by any multiplex amplification.

The target nucleic acids can be, for example, multiple strains of methicillin resistant *Staphylococcus aureus* (MRSA). For such a method of amplifying multiple strains of methicillin resistant *Staphylococcus aureus*, or for a kit comprising reagents for amplifying multiple strains of methicillin resistant *Staphylococcus aureus*, the first target nucleic acid can be one present in a first strain of methicillin resistant *Staphylococcus aureus* that is specific to that first strain and the second target nucleic acid can be one present in a second strain of methicillin resistant *Staphylococcus aureus* that is specific to that second strain. Third, fourth, etc. strains can similarly be included, as desired. The first and/or the second promoter oligonucleotide (P1 primer) can be blocked at its 3' end. One of skill in the art can optimize for the specific strains selected to be detected in an given reaction, the optimal use of the blocking moiety on the promoter oligonucleotides, i.e., which to block and which not to block, given the teachings herein.

Furthermore, nucleotides in any selected oligonucleotide primer or probe may be modified by addition of chemical groups, or substitution of individual residues by analogues (e.g., 2'-O-methoxy versions). Additional such modified nucleotides are known in the art; some examples include hydroxymethyl nucleotides, methylated nucleotides, fluorinated nucleotides, alpha thio phosphate nucleotides, amine-modified nucleotides, methoxy nucleotides, carboxymethyl nucleotides, thio nucleotides, inosine, dihydrouridine, psuedouridine, wybutosine, queuosine, C7dGTP. Additional modified nucleotides are found in U.S. Pat. Nos. 5,405,950 and 5,633,364 (both, Mock and Lovern). Particularly useful modifications are those that increase the melting temperature of a nucleic acid hybrid.

EXAMPLES

Primer Synthesis

Oligonucleotides for use as P1 and/or P2 primers or probes were synthesized by standard automated DNA synthesis methods, known in the art. Primers were purified by PAGE and HPLC. Because of the means by which the dabcyl-, dabsyl-and amino-blocked primers are made, essentially all primers utilized in the Examples should have the blocking moiety attached. For all P1 primers, the following sequences were used as the T7 Polymerase promoter (5') region of the primer: AATTTAATACGACTCACTATAGGG (SEQ ID NO:1); AATTCTAATACGACTCACTATAGGG (SEQ ID NO:2). Dabcyl, where utilized, was attached to the 3' end of the oligonucleotide during automated DNA synthesis using a dabcylated 3'-controlled pore glass (CPG) support. Dabsyl is similarly attached. Amino, where utilized, was attached during the first step of primer synthesis, similar to the dabcyl-blocked primer synthesis. Primers were then purified by PAGE and/or HPLC.

Amplification

Standard NASBA assays were performed to determine the presence or absence of a selected target in a sample, with any specific modifications noted within the Example.

Example 1

HSV-Enterovirus Multiplex NASBA with 3'-Blocked Primers

To test the effect of blocked p1 primers, a multiplex NASBA of HSV and Entero virus was performed. Amplification was performed using standard NASBA reagents (40 mM Tris-HCl pH 8.5, 12 mM $MgCl_2$, 90 mM KCl, 15% v/v DMSO, 5 mM DTT, 1 mM each dNTP, 2 mM ATP, 2 mM CTP, 2 mM UTP, 1.5 mM GTP, 0.5 mM ITP, 0.2 µM of each primer (forward primer (P1) and reverse primer (P2), Table 1), 0.1 µM molecular beacon probe (Table 1) and 1 unit Sal1 restriction enzyme. The mixture was incubated for 15 min at 41° C. to perform the restriction enzyme digestion for the HSV target, 5 min at 95° C. to denature the target and inactivate the Sal 1 enzyme, and for 3 min at 41° C. to hybridize the P1 primer to the target. Subsequently, NASBA enzymes (0.08 units RNase H, 32 units T7 RNA polymerase, 6.4 units AMV reverse transcriptase, 2.1 µg BSA in presence of 0.88M sorbitol (final concentration)) were added, the reaction mixture was mixed by gently vortexing and short centrifugation, and the amplification and real-time detection was started. The reaction mixture was incubated at 41° C. in the NucliSens EasyQ Analyzer (NucliSens, BioMérieux) for 150 minutes with fluorescence monitoring every 30 seconds. The reactions were excited at 485 nm (FAM) and 578 nm (ROX) and the emission signal was measured at 518 nm (FAM) and 604 nm (ROX).

An input of 200 cps in vitro transcribed Entero virus internal control (IC) RNA or 100 cps HSV DNA (plasmid containing part of HSV sequence) was used in amplification. The Entero reference p1 (Entero ref p1, Table 1) and reference p2 (Entero ref p2, Table 1) were used in combination with the Entero IC specific beacon (Entero IC beacon, Table 1). The standard HSV p2 (HSV ref p2, Table 1) and HSV beacon (HSV1 WT beacon) were added to the Entero primers in combination with the non-blocked (HSV ref p1, Table 1) or the 3' DabSyl blocked HSV p1 (HSV ref p1-block, Table 1).

Figure 3:
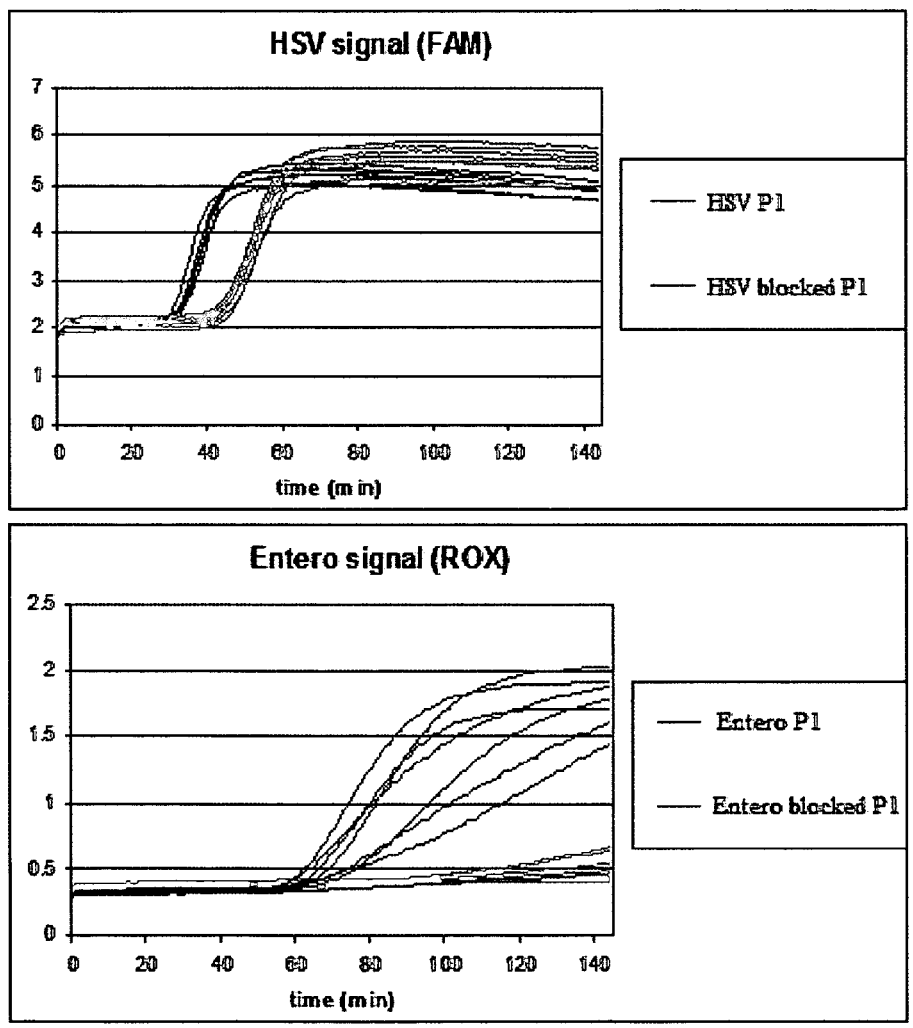
FIG. 3 shows Multiplex Entero-HSV NASBA amplification. An input of 200 cps Entero IC RNA or 100 cps HSV DNA was used in amplification. Amplification was performed in presence of the standard Entero primers and beacon (Entero ref p1 & p2, Entero IC beacon, Table 1), the standard HSV p2 (HSV ref p2, Table 1), HSV beacon (HSV WT MB) in combination with the non-blocked HSV p1 or the 3' DabSyl blocked HSV p1 (HSV ref p1, Table 1).

Results are presented in FIG. 3. Addition of the non-blocked HSV ref p1 results in no Entero amplification at all, while addition of the 3' blocked HSV ref p1 results in good Entero amplifications. HSV amplification is not inhibited by the presence of the entero primers. This indicates that the use of blocked p1 primers can improve multiplex NASBA.

TABLE 1

Primer sequences of p1 primers, p2 primers and molecular beacons

| | Sequence 5'->3' | SEQ ID NO |
|---|---|---|
| HSV primers & beacon | | |
| HSV ref p1 | AATTCTAATACGACTCACTATAGGG AGA CCAGGGCCCTGGAGGTGCGG | 7 |
| HSV ref p1-block | HSV ref p1 with 3' DabSyl group | 7 |
| HSV ref p2 | ACGTTCACCAAGCTGCTGCT | 8 |
| HSV WT MB (gen WT3) | cgatcg GAAAAAGTACATCGGCGTCATCT cgatcg (5' FAM 3' dabSyl) | 9 |
| Entero primers & beacon | | |
| Entero ref p1 | AATTCTAATACGACTCACTATAGGG CACCGGATGGCCAATCCA | 3 |
| Entero ref p2 | GATGCAAGGTCGCATATGAG GGTGTGAAGAGCCTATTGAG | 4 |
| Entero WT MB | CcatgcgTCCTCCGGCCCCTGAATGCGcgcatgg 5' FAM 3' dabSyl | 5 |
| Entero IC beacon | cgatgc GCAAAGTATCATCCCTCCAG gcatcg (5' ROX 3' dabSyl) | 6 |

\* Note:
Target specific sequences in bold; T7 promoter sequences in italic; non-target stem sequences in lower case; 2'-O-Methoxy nucleotides underlined

Example 2

Use of Blocked p1 Primers in Enterovirus-HIV Multiplex NASBA

From earlier performed multiplex NASBA experiments it is known that addition of only a second primer set can result in inhibition of the reaction. To test the effect of blocked p1 primers, a multiplex of HIV with Entero virus was performed. Entero virus amplification was performed in presence of a standard HIV p2 primer and a non-blocked or blocked HIV p1 primer.

Standard HIV Amplification Conditions

HIV particles, from cell culture, lysed with lysis buffer (NucliSens Extraction reagents, BioMérieux) were used as input material for amplification. A subtype B sample was used: WRS (Working Reference Standard) defined in International Units (IU) of which inputs of 500, 50 and 10 IU were used. Amplification was performed using standard NASBA reagents (40 mM Tris-HCl pH 8.5, 12 mM $MgCl_2$, 70 mM KCl, 15% v/v DMSO, 5 mM DTT, 1 mM each dNTP, 2 mM ATP, 2 mM CTP, 2 mM UTP, 1.5 mM GTP, 0.5 mM ITP, 0.2 µM of each primer (forward primer (P1) and reverse primer (P2)) and 0.01 µM molecular beacon probe. The mixture was incubated for 2 min at 65° C. to denature the RNA and for 2 min at 41° C., to hybridize the P1 primer to the target. Subsequently, NASBA enzymes (0.08 units RNase H, 32 units T7 RNA polymerase, 6.4 units AMV reverse transcriptase and 2.1 µg BSA) were added, the reaction mixture was mixed by gently vortexing and short centrifugation, and the amplification and real-time detection was started. The reaction mixture was incubated at 41° C. in the NucliSens EasyQ Analyzer (NucliSens, BioMérieux) for 60 minutes with fluorescence monitoring every 30 seconds. The reactions were excited at 485 nm and the emission signal was measured at 518 nm.

Amplification was performed in conditions optimal for Enterovirus: the same standard HIV NASBA conditions as described in standard HIV conditions above except that a higher KCl concentration was used (100 mM) and the reaction was performed in the presence of 0.5M sorbitol. In vitro transcribed Entero virus RNA, 5000, 500, 50 and 5 cps, was used as input. The Entero reference p1 (Entero ref p1, Table 2) and reference p2 (Entero ref p2, Table 2) were used in combination with the Entero-specific beacon (Entero WT beacon, Table 2). The standard HIV p2 (HIV ref p2, Table 2) was added to the Entero reaction in combination with non-blocked HIV ref p1 (Table 2) or 3' DabSyl-blocked HIV ref p1 (Table 2).

TABLE 2

Primer sequences of the p1 primers (with and without a 3' DabSyl block), p2 primers and Molecular beacons, used for NASBA amplification.

| p1 primers | Target-specific Sequence 5'->3' | SEQ ID NO. | HIV Subtype Based On |
|---|---|---|---|
| HIV p1 primers | | | |
| HIV ref p1 | T7-CCTGCTATGTCACTTCCCCTTGGTTCTCT | 3 | B |
| HIV ref p1 block | "HIV ref p1" with 3' DabSyl group | | B |
| HIV type F p1 | T7-CCAGCTATATCACTTCCCCTAGGTTCCCT | 4 | F |

TABLE 2-continued

Primer sequences of the p1 primers (with and without a 3' DabSyl block), p2 primers and Molecular beacons, used for NASBA amplification.

| p1 primers | Target-specific Sequence 5'->3' | SEQ ID NO. | HIV Subtype Sequence Based On |
|---|---|---|---|
| HIV type F p1 block | "HIV type F p1" with 3' DabSyl group | | F |
| HIV ref p1 Short 1 | T7-CCTGCTATGTCACTTCCCCT | 5 | B |
| HIV ref p1 Short 1 block | "HIV ref p1 Short 1" with 3' DabSyl group | | B |
| HIV ref p1 Short 2 | T7-TCACTTCCCCTTGGTTCTCT | 6 | B |
| HIV ref p1 Short 2 block | "HIV ref p1 Short 2" with 3' DabSyl group | | B |
| T7 Promoter sequence for all HIV p1 primers (at 5'end of target-specific sequence) | *AATTCTAATACGACTCACTATAGGG AGA*- target-specific sequence | 2 | |
| HIV p2 primer | | | |
| HIV ref p2 | AGTGGGGGGACATCAAGCAGCCATGCAAA | 7 | |
| HIV WT molecular beacon | | | |
| HIV WT MB (Me8) | ctatccc ATC<u>AATGAGGA</u>I<u>GCT</u>GCAGA<u>I</u>T gggatag<br>5' FAM 3' dabSyl<br>2'-O-Methoxy nucleotides underlined<br>Non-target "stem" sequences in lower case | 8 | |
| Entero primers & beacon | | | |
| Entero ref p1 | *AATTCTAATACGACTCACTATAGGG*<br>CACCGGATGGCCAATCCA<br>Non-target specific sequence (T7Promoter) in italic | 9 | |
| Entero ref p2 | *GATGCAAGGTCGCATATGAG* GGTGTGAAGA<br>GCCTATTGAG<br>Non-target specific sequence in italic | 10 | |
| Entero WT MB | CcatgcgTCCTCCGGCCCCTGAATGCGcgcatgg<br>5' FAM 3' dabSyl<br>Non-target "stem" sequences in lower case | 11 | |

Figure 4:
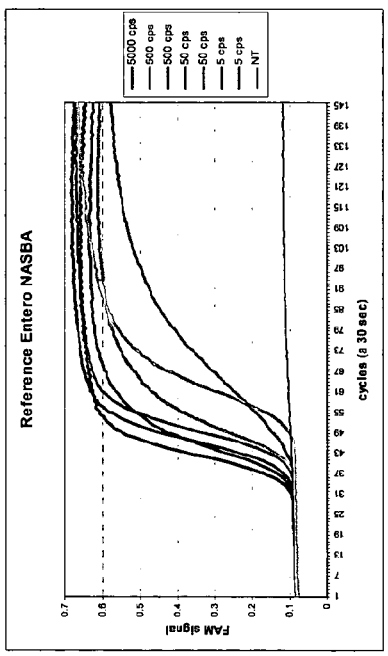
FIG. 4 shows Entero NASBA amplification in presence of HIV primers. A dilution series of Entero WT transcript, 5000, 500, 50 and 5 cps, was used as input. A sample without template (NT) was used as negative control. In the reference reactions only Entero primers and beacon are present. In the other reactions a 3' DabSyl blocked or unblocked HIV ref p1 primer was added, both in combination with the standard HIV ref p2 primer.
Figure 4:
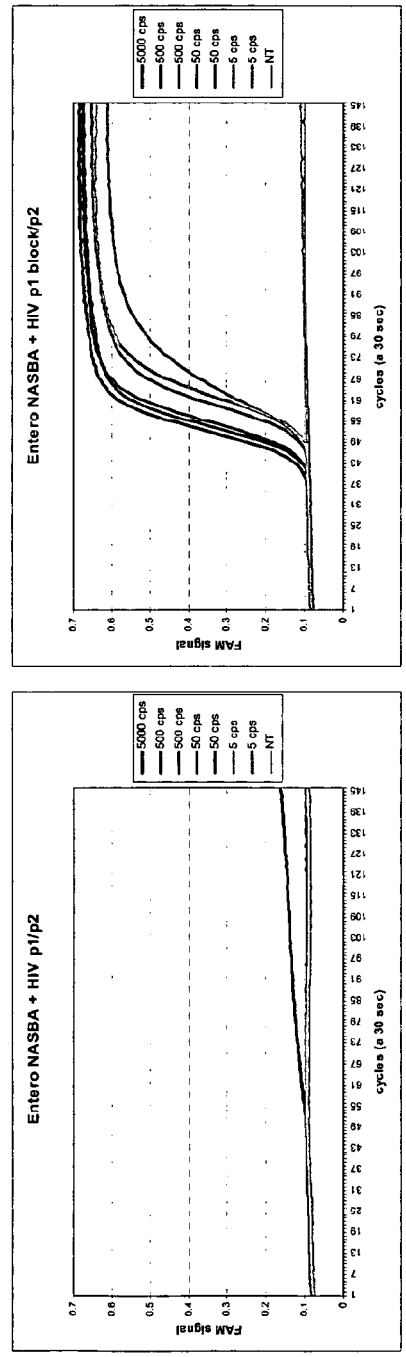

Results are presented in FIG. 4. Addition of the normal non-blocked HIV ref p1 (and standard HIV ref p2) results in no Entero amplification at all. Addition of a 3'-blocked HIV ref p1 (and standard HIV p2) results in good Entero amplifications comparable to the reference reactions in which only Entero primers are present. This indicates that the use of blocked p1 primers can improve multiplex NASBA.

Example 3

Detection of 3'-Blocked HIV in Multiplex NASBA

An additional experiment was performed to see if also HIV could be amplified in presence of the Entero primers. Multiplex amplification was performed with the standard Entero primers as described above, 3' DabSyl-blocked HIV ref p1, standard HIV ref p2 and a HIV specific molecular beacon (HIV WT MB, Table 1). An input of 50 IU WRS of HIV subtype B (5 samples) was used as input. Results show that HIV amplification with a 3' blocked p1 primer can be performed in presence of the Entero primers (FIG. 5). This provides additional applications in which the use of blocked p1 primers can improve multiplex NASBA.

Throughout this application, various publications are referenced. The disclosures of these publications in their entireties are hereby incorporated by reference into this application in order to more fully describe the state of the art to which this invention pertains.

While there have been herein described what are presently believed to be the preferred embodiments of the present invention, those skilled in the art will realize that other and further embodiments can be made without departing from the spirit and scope of the invention, and it is intended to include all such further modifications and changes as come within the true scope of the invention.

What is claimed is:

1. A method of performing a specific transcription-based amplification reaction of a selected first target nucleic acid in a sample, in a reaction wherein reagents specific for amplification of more than one target nucleic acid are present, comprising:
   (1) contacting the sample with at least a first oligonucleotide pair for amplifying a first target nucleic acid and a second oligonucleotide pair for amplifying a second nucleic acid target,
      (a) the first oligonucleotide pair consisting of a first promoter oligonucleotide having a 5' end and a 3' end and being non-blocked, the first promoter oligonucleotide comprising, at the 5' end, an RNA polymerase promoter sequence, and 3' of the RNA polymerase promoter sequence, a sequence complementary to a first target portion of the first target nucleic acid and a first primer oligonucleotide that is not blocked comprising a sequence homologous to a second target portion of the first target nucleic acid, which second target portion is 5' of the first target portion of the first target nucleic acid, and
      (b) a second oligonucleotide pair consisting of a second promoter oligonucleotide having a 5' end and a 3' end, the second promoter oligonucleotide comprising, at the 5' end, an RNA polymerase promoter sequence, and 3' of the RNA polymerase promoter sequence, a sequence complementary to a first target portion of a second target nucleic acid wherein further, the second promoter oligonucleotide comprises, at the 3' end, a blocking moiety such that extension therefrom is essentially prohibited and a second primer oligonucleotide that is not blocked comprising a sequence homologous to a second target portion of the second target nucleic acid, which second target portion is 5' of the first target portion of the second target nucleic acid; and
   (2) providing selected reagents and conditions for transcription-based amplification, thereby performing a specific transcription-based amplification reaction of a selected first target nucleic acid in a sample, in a reaction wherein reagents specific for amplification of more than one target nucleic acid are present.

2. The method according to claim 1, wherein the blocking moiety remains present at the 3'end of the second promoter oligonucleotide at any selected amplification reaction temperature.

3. The method according to claim 1, wherein the conditions for transcription-based amplification are optimized for the first target nucleic acid.

4. The method according to claim 1, wherein the conditions for transcription-based amplification are optimized for the second target nucleic acid.

5. The method according to claim 1, wherein the blocking moiety on the second promoter oligonucleotide remains present at the 3'end of the oligonucleotide at any selected amplification reaction temperature.

6. The method according to claim 1, further comprising contacting the sample with a third oligonucleotide pair, the third oligonucleotide pair consisting of a third promoter oligonucleotide having a 5 end and a 3' end, the third promoter oligonucleotide comprising, at the 5'end, an RNA polymerase promoter sequence, and 3' of the RNA polymerase promoter sequence, a sequence complementary to a first target portion of a third target nucleic acid and a third primer oligonucleotide comprising a sequence homologous to a second target portion of the third target nucleic acid, which second target portion is 5 of the first target portion of the third target nucleic acid.

7. The method according to claim 1, wherein the blocking moiety is dabsyl.

8. The method according to claim 1, wherein the blocking moiety is dabcyl.

9. The method according to claim 1, wherein the blocking moiety is an amino group.

10. The method according to claim 1, wherein the blocking moiety is a phosphate.

11. The method according to claim 1, wherein the sample is further contacted with a detectably labeled first probe oligonucleotide homologous to a third target portion of the first target nucleic acid, which third target portion is located between the first target portion and a second target portion.

12. The method according to claim 11, wherein the sample is further contacted with a detectably labeled second probe oligonucleotide homologous to a third target portion of the second target nucleic acid, which third target portion is located between the first target portion and a second target portion.

13. The method according to claim 1, wherein the first and second target nucleic acids are nucleic acids of two strains of the same organism.

14. The method according to claim 1, wherein the first and second target nucleic acids are nucleic acids of different organisms.

15. The method according to claim 1, wherein the first and second target nucleic acids nucleic acid is DNA or RNA.

16. The method according to claim 1, wherein the selected reagents for transcription-based amplification reaction comprise:
   i) an enzyme having reverse transcription activity,
   ii) at least one enzyme having RNase H activity,
   iii) an enzyme having RNA polymerase activity, and
   iv) sufficient amounts of dNTPs and rNTPs.

17. The method according to claim 1, wherein the second promoter is functional with the same polymerase as the promoter of the first promoter oligonucleotide.

18. The method according to claim 1, wherein the first target nucleic acid is present in a first strain of methicillin resistant *Staphylococcus aureus* and the second target nucleic acid is present in a second strain of methicillin resistant *Staphylococcus aureus*.

19. The method according to claim 1, wherein the second target nucleic acid is present in HIV-1.

\* \* \* \* \*

UNITED STATES PATENT AND TRADEMARK OFFICE
CERTIFICATE OF CORRECTION

PATENT NO. : 8,822,152 B2  Page 1 of 1
APPLICATION NO. : 12/513955
DATED : September 2, 2014
INVENTOR(S) : van de Wiel et al.

It is certified that error appears in the above-identified patent and that said Letters Patent is hereby corrected as shown below:

In the Claims:
Column 26, Claim 6, Line 42: Please correct "having a 5 end"
to read -- having a 5' end --
Line 49: Please correct "portion is 5 of the first"
to read -- portion is 5' of the first --

Column 27, Claim 15, Lines 10 and 11: Please correct "the first and second target"
to read -- the first and the second target --

Signed and Sealed this
Tenth Day of February, 2015

Michelle K. Lee
*Deputy Director of the United States Patent and Trademark Office*